United States Patent [19]
Gruter et al.

[11] Patent Number: 6,117,811
[45] Date of Patent: Sep. 12, 2000

[54] CYCLOPENTADIENE COMPOUND SUBSTITUTED WITH LINEAR GROUPS

[75] Inventors: Gerardus J. M. Gruter, Maastricht, Netherlands; Johannes A. M. van Beek, Mountain View, Calif.; Richard Green, Geleen; Edwin G. Ijpeij, Sittard, both of Netherlands

[73] Assignee: DSM N.V., Heerlen, Netherlands

[21] Appl. No.: 09/184,066

[22] Filed: Nov. 2, 1998

Related U.S. Application Data

[63] Continuation of application No. PCT/NL97/00232, Apr. 28, 1997.

[30] Foreign Application Priority Data

May 3, 1996 [NL] Netherlands ............................ 1003005

[51] Int. Cl.$^7$ ................................ B01J 31/18; B01J 31/22
[52] U.S. Cl. ......................... 502/155; 502/103; 502/152; 526/161; 526/943; 526/160; 556/53; 556/13
[58] Field of Search ............................... 556/53; 502/103, 502/152, 155; 526/161, 943

[56] References Cited

U.S. PATENT DOCUMENTS

| | | | |
|---|---|---|---|
| 5,523,435 | 6/1996 | Lisowsky | 556/11 |
| 5,554,795 | 9/1996 | Frey et al. | 568/8 |
| 5,563,284 | 10/1996 | Frey et al. | 556/53 |

FOREIGN PATENT DOCUMENTS

| | | |
|---|---|---|
| 0 416 815 A2 | 3/1991 | European Pat. Off. . |
| 0 728 724 | 8/1996 | European Pat. Off. . |
| 0 728 769 A1 | 8/1996 | European Pat. Off. . |
| 0 728 770 A1 | 8/1996 | European Pat. Off. . |
| 43 03 647 | 8/1994 | Germany . |
| 864198 | 3/1961 | United Kingdom . |
| WO 95/00562A | 1/1995 | WIPO . |
| WO 96/13529 | 5/1996 | WIPO . |

OTHER PUBLICATIONS

Szymoniak et al., "New Heterodifunctional Ligands for Organotransiton–Metal Chemistry: . . . ", Journal of Organic Chemistry, 1990, vol. 55, pp. 1429–1432.

Ying Mu et al., "Use of Alkane Elimination in the One–step Synthesis of Organscandium Complexes Containing a New Multidentate Cyclopentadienyl Ligand", Organometallics, 1996, vol. 15, pp. 2720–2726.

Chemical Abstracts, vol. 123, No. 13 (Sep. 1995), Abstract No. 169881g.

Weinheim DE, K. Hafner et al., "Synthesen und Reaktionen von Fulvenaldehyden", Chemische Berichte, 1963, vol. 661, pp. 52–75.

G. Kresze et al., "Substituierte Cyclopentadiene und ihre Diels–Alder–Reaktionen", Chemische Berichte, 1963, vol. 666, pp. 45–53.

Krut'ko, D.P. et al., "Tetramethyl(2–methylthioethyl)cyclopentadienyl Complexes of Zirconium(IV): Synthesis, . . . Solutions", Russian Chemical Bulletin, 1996, vol. 45, No. 4, pp. 940–949.

Ulrich Siemeling, "$C_5Me_4(CH_2)_3OMe$: A Tentacle–bearing Cyclopentadienyl Ligand and Its Use in Complex Chemistry", J. Chem. Soc. Commun., 1992, vol. 18, pp. 1335–1336.

R. Allen Williams et al., 'Encapsulated Alkaline–Earth Metallocenes. Synthesis, Solution Behavior, and Solid–State Structures of . . . ', Journal of the American Chemical Society, vol. 113, No. 13, Jun. 19, 1991, pp 4843–4851.

Clifford G. Venier et al., 'D–tert–butylcyclopentadiene and Tri–tert–butylcyclopentadiene', Journal of the American Chemical Society, vol. 112, No. 7, Mar. 28, 1990.

Eckehard V. Dehmlow et al., 'Phase Transfer Catalyzed tert–Alkylations of Cyclopentadiene and Indene: Indications for Set Processess', Tetrahedron Letters, vol. 32, No. 41, Oct. 1991.

R.H. Chung, et al., "1–Isopropyl–4–methylenebicyclo [3.1.0]hex–2–ene. Synthesis and reactions", J. Amer. Chem. Soc., vol. 94(7), pp. 2183–2187, 1972.

G. Moran et al., "Formation of a fulvene by trimerisation of an alkyne at a Rhodium centre; . . . ", Journal of Organometallic Chemistry, vol. 250, 1983, pp. C15–C20.

T. Jeffrey Clark et al., "Regioselective synthesis of dialkyl–1,3–cyclopentadienes via novel 2–alkyl–6,6–dialkylfulvenes" Synlett (1990), (10), 589–90.

T. Leigh, "Ferrocene Derivatives containing Tertiary Alkyl Groups. Synthesis by the Friedel–Crafts and Other Methods", Journal of the Chemical Society, 1964, Letchworth GB, pp. 3294–3302.

R.R. Schrock et al., "Formation of Cyclopentadienyl Complexes from Tungstenacyclobutadiene Complexes and the X–ray Crystal Structure of an eta–3–Cyclopropenyl Complex, W[C(CMe3)C(Me)C(Me)] (Me2NCH2CH2NMe2)Cl3", Organometallics, vol. 3, No. 10, 1984, pp. 1574–1583.

H. Van Der Heijden et al., "Reactions of the Trimetallic Neopentylidene Complex [{Cl2(MeOCH2CH20Me)Ta(mu–CCMe3)}2Zn(mu–Cl)2] with Alkynes. A Structural Study of [(eta5–C5(t–Bu)(CH2CMe3)2(CH2CMe2CH2)2)TaC12]", Organometallics, vol. 4, No. 10, 1985, pp. 1847–1853.

Sappa Enrico et al., "Mass spectral investigations on sigma–pi bonded binuclear alkyne–carbonyl derivatives of iron. Fe2(CO)5/C2RR')3(C)) and Fe2(CO)6/C2RR')3 complexes", Chemical Abstracts, vol. 91, No. 9 (Aug. 27, 1979, Abstract No. 73791x.

Bensley, Jr. et al.; "Synthesis of $[C_5(CH_3)_4H]CH_2CH_2CH_2P(C^6H_5)_2$: A Novel . . . Functionality"; J. Org. Chem. 1988, vol. 53, pp. 4417–4419.

Balakrishnan, P.V. et al; (Pentamethyl–cyclopentadiene-)palladium Complexes; J. Chem. Soc. (A), Inorg. Phys. Theor.; 1971, pp. 1721–1725.

*Primary Examiner*—David W. Wu
*Assistant Examiner*—Caixia Lu
*Attorney, Agent, or Firm*—Pillsbury Madison & Sutro Intellectual Property Group

[57] ABSTRACT

Polysubstituted cyclopentadiene compound, wherein at least one substituent is of the form —RDR'$_n$, where R is a bonding group between the cyclopentadiene and the DR'$_n$ group, D is a hetero atom chosen from group 15 or 16 of the Periodic Table of the Elements, R' is a substituent and n is the number of R' groups bonded to D, and in which at least one further substituent is a linear alkyl group comprising at least 2 carbon atoms.

6 Claims, No Drawings

CYCLOPENTADIENE COMPOUND SUBSTITUTED WITH LINEAR GROUPS

This is a Continuation of International Appln. No. PCT/NL/97/00232 filed Apr. 28, 1997 which designated the U.S.

The invention relates to a polysubstituted cyclopentadiene compound.

Cyclopentadiene compounds are generally used as a ligand in metal complexes which are active as catalyst components, in particular for the polymerization of olefins. Depending on the metal, its valency state and the ligands used, these complexes appear to be of varying suitability for specific applications.

In J. of Organomet. Chem., 479 (1994), 1–29 an overview is provided of the influence of the substituents on cyclopentadiene as a ligand in metal complexes. Here it is observed, on the one hand, that the chemical and physical properties of metal complexes can be varied over a wide range by the specific choice of the substituents on the cyclopentadiene ring. On the other hand, it is stated that no predictions can be made concerning the effect to be expected of specific substituents.

The most commonly used cyclopentadiene compounds are unsubstituted cyclopentadiene or cyclopentadiene substituted with one to five methyl groups. However, when used as a ligand in metal complexes in which the metal is not in the highest valency state, so in which the metal is for instance Ti(III), Hf(III), Zr(III) or V(IV), these appear to give catalyst components of a low to very low activity, in particular for olefin polymerization.

In the above-mentioned overview article in the J. of Organomet. Chem. from 1994 it is even observed that 'An important feature of these catalyst systems is that tetravalent Ti centres are required for catalytic activity'. In this context it should be kept in mind that Ti is exemplary of the metals that are suitable as metal in the commonly used cyclopentadienyl-substituted metal complexes.

In the following, cyclopentadiene will be abbreviated as Cp. The same abbreviation will be used for a cyclopentadienyl group if it is clear, from the context, whether cyclopentadiene itself or its anion is meant.

The term 'olefins' here and in the following refers to α-olefins, diolefins and other unsaturated monomers. Where the term 'polymerization of olefins' is used, this refers both to the polymerization of a single type of olefinic monomer and to the copolymerization of two or more olefins.

The aim of the invention now is to provide Cp compounds which, when used as a ligand in a metal complex in which the metal is not in the highest valency state, give catalyst components with a higher activity than those with the usual Cp-containing ligands.

This object is achieved according to the invention in that at least one substituent is of the form —RDR'$_n$, where R is a bonding group between the Cp and the DR'$_n$ group, D is a hetero atom chosen from group 15 or 16 of the Periodic Table of the Elements, R' is a substituent and n is the number of R' groups bonded to D, and in that at least one further substituent is a linear alkyl group comprising at least 2 carbon atoms.

Surprisingly it is found that when Cp compounds thus substituted are used as a ligand in the above-described metal complexes, they give catalyst components that have a higher activity in the polymerization of olefins, in particular in ethylene polymerization, than the known Cp compounds. The compound preferably contains at least two linear alkyl groups with at least two carbon atoms as substituents, because this gives a further increase in activity compared with the Cp compound that is monosubstituted with a linear alkyl group.

From DE-A-4303647 tetramethyl- and tetraethyl-substituted cyclopentadienes are known in which D is O, N or S and in which R is a methylene or ethylene group. From J. Org. Chem., 1990, 55, 1429–1435 a tetramethyl-substituted cyclopentadiene is known in which the group RDR'$_n$ is a diphenylphosphinyl or an ethylene diphenylphosphinyl.

These publications do not provide any indication as to the particular suitability of the Cp compounds according to the invention as ligands in metal complexes with metals that are not in the highest valency state.

Corresponding complexes in which the Cp compound has not been substituted as described in the foregoing, appear to be unstable or, if they have been stabilized in another way, to yield less active catalysts than the complexes with substituted Cp compounds according to the invention, in particular in the polymerization of α-olefins.

Further it appears that the Cp compounds according to the invention can stabilize highly reactive intermediates such as organometal hydrides, organometal boron hydrides, organometal alkyls and organometal cations. Moreover, the metal complexes containing Cp compounds according to the invention appear to be suitable as stable and volatile precursors for use in metal chemical vapour deposition.

In fact the Cp compounds according to the invention can also be used as ligands to metals which are in their highest valency state and yield special advantages then in specific cases.

The linear alkyl groups comprising at least two carbon atoms may be identical or different from each other. The substituted Cp compound preferably contains 2, 3 or 4 linear alkyl groups as substituents, because with the number of these substituents the activity of the catalyst made from it appears to increase. The linear alkyl groups do not contain a hetero atom from group 16 of the Periodic Table of the Elements. Groups that are suitable as linear substituents are for instance methyl, ethyl, propyl, butyl, pentyl, hexyl, heptyl, octyl, nonyl, decyl, undecyl, dodecyl, pentadecyl, hexadecyl, octadecyl, eicosyl, docosyl, dodecyl, di-, tri- and tetravinyl, trifluoromethyl, chloromethyl, dichloromethyl, trichloromethyl, 2-chloroethyl, 3-chloropropyl, 5-chloropentyl and 4-butenyl. Cp compounds that are tetra-substituted with ethyl- and/or propyl groups are preferred.

Besides these linear alkyl groups, whose presence is required within the scope of the invention, further substituents can also be present, for instance branched and cyclic alkyl groups, alkenyl and aralkyl groups. Apart from carbon and hydrogen, one or more hetero atoms from groups 14–17 of the Periodic System of the Elements can also be present, for example O, N, Si or F. Examples of suitable groups are iso-propyl, sec-butyl, -pentyl, -hexyl and -octyl, tert-butyl and higher homologues, cyclohexyl, benzyl, phenyl, para-tolyl and trimethylsilyl.

For the Periodic Table, see the new IUPAC notation to be found on the inside of the cover of the Handbook of Chemistry and Physics, 70th Edition, 1989/1990.

Substituted Cp compounds can, for instance, be prepared by reacting a halide of the substituting compound in a mixture of the Cp compound and an aqueous solution of a base in the presence of a phase transfer catalyst. By Cp compounds are understood Cp as such and Cp which is already substituted in at least one position, with the possibility of two substituents forming a closed ring. The process to be further described in the following thus enables unsubstituted compounds to be converted to mono- or polysubstituted ones, but also already mono- or polysubstituted Cp-based compounds to be substituted further, which can be followed by ring closure. A virtually equivalent quantity with respect to the Cp compound of the halogenated substituting compounds can be used. An equivalent quantity is understood as a quantity in moles which corresponds to the desired substitution multiplicity, for example 2 mol per mole of Cp compound if disubstitution with the substituent in question is intended.

Depending on the size and the associated steric hindrance of the substituting compounds it is possible to obtain trisubstituted to hexasubstituted Cp compounds. The number of substituents to be applied in this way is 1–4 for the Cp compounds according to the invention, apart from any other substituents to be substituted in remaining free positions, as defined in the foregoing. The substituents are preferably used in the process in the form of their halides and more preferably in the form of their bromides. If bromides are used a smaller quantity of phase transfer catalyst is found to be sufficient, and a higher yield of the compound aimed for is found to be achieved.

By means of this process it is also possible, without intermediate isolation or purification, to obtain Cp compounds which are substituted by specific combinations of substituents. Thus, for example, disubstitution with the aid of a certain halide of a substituting compound can first be carried out and in the same reaction mixture a third substitution can be carried out by a different substituent, by adding a second, different halide of a substituting compound to the mixture after a certain time. This can be repeated, so that it is also possible to prepare Cp derivatives having three or more different substituents.

The substitution takes place in a mixture of the Cp compound and an aqueous solution of a base. The concentration of the base in the solution is in the range between 20 and 80 wt. %. Hydroxides of an alkali metal, for example K or Na are highly suitable as a base. The base is present in an amount of 5–60, preferably 6–30, mol per mole of Cp compound. It has appeared that a substantial reduction of the reaction time can be achieved if the solution of the base is refreshed during the reaction, for instance by first mixing the solution of the base with the other components of the reaction mixture and after some time isolating the aqueous phase and replacing it by a fresh quantity of solution of the base. The substitution takes place at atmospheric or elevated pressure, for instance up to 100 MPa, which higher level is applied in particular if volatile components are present. The temperature at which the reaction takes place may vary within wide limits, for instance from –20 to 120° C., preferably between 10 and 50° C. Starting up the reaction at room temperature is usually suitable, after which the temperature of the reaction mixture can rise due to the heat released in the reactions.

The substitution takes place in the presence of a phase transfer catalyst which is able to transfer OH-ions from the aqueous phase to the organic phase containing Cp compound and halide, the OH-ions reacting in the organic phase with a H-atom which can be split off from the Cp compound. Possible phase transfer catalysts to be used are quaternary ammonium, phosphonium, arsonium, stibonium, bismuthonium, and tertiary sulphonium salts. More preferably, ammonium and phosphonium salts are used, for example tricaprylmethylammonium chloride, commercially available under the name Aliquat 336 (Fluka AG, Switzerland; General Mills Co., U.S.A.) and Adogen 464 (Aldrich Chemical Co., USA). Compounds such as benzyltriethylammonium chloride (TEBA) or benzyltriethylammonium bromide (TEBA-Br), benzyltrimethylammonium chloride, benzyltrimethylammonium bromide or benzyltrimethylammonium hydroxide (Triton B), tetra-n-butylammonium chloride, tetra-n-butylammonium bromide, tetra-n-butylammonium iodide, tetra-n-butylammonium hydrogen sulphate or tetra-n-butylammonium hydroxide and cetyltrimethylammonium bromide or cetyltrimethylammonium chloride, benzyltributyl-, tetra-n-pentyl-, tetra-n-hexyl- and trioctylpropylammonium chlorides and their bromides are likewise suitable. Usable phosphonium salts include, for example, tributylhexadecylphosphonium bromide, ethyltriphenylphosphonium bromide, tetraphenylphosphonium chloride, benzyltriphenylphosphonium iodide and tetrabutylphosphonium chloride. Crown ethers and cryptands can also be used as a phase transfer catalyst, for example 15-crown-5, 18-crown-6, dibenzo-18-crown-6, dicyclohexano-18-crown-6, 4,7,13,16,21-pentaoxa-1,10-diazabicyclo[8.8.5]tricosane (Kryptofix 221), 4,7,13,18-tetraoxa-1,10-diazabicyclo[8.5.5]eicosane (Kryptofix 211) and 4,7,13,16,21,24-hexaoxa-1,10-diazabicyclo[8.8.8]-hexacosane ("[2.2.2]") and its benzo derivative Kryptofix 222 B. Polyethers such as ethers of ethylene glycols can also be used as a phase transfer catalyst. Quaternary ammonium salts, phosphonium salts, phosphoric acid triamides, crown ethers, polyethers and cryptands can also be used on supports such as, for example, on a crosslinked polystyrene or another polymer. The phase transfer catalyst is used in an amount of 0.01–2, preferably 0.05–1 equivalents on the basis of the amount of Cp-compound.

The various components can be supplied to the reactor in various sequences in the implementation of the process.

Upon completion of the reaction the aqueous phase and the organic phase containing the Cp compound are separated. When necessary, the Cp compound is recovered from the organic phase by fractionated distillation.

A group of the form —RDR$'_n$ can subsequently be substituted on the Cp compound thus substituted.

The R group constitutes the bond between the Cp and the DR$'_n$ group. The length of the shortest bond between the Cp and D is critical in that, if the Cp compound is used as a ligand in a metal complex, it determines the accessibility of the metal to the DR$'_n$ group, a factor which facilitates the desired intramolecular coordination. If the R group (or bridge) is too short, the DR$'_n$ group may not be able to coordinate properly owing to ring tension. R is at least one atom long.

The R' groups can each separately be a hydrocarbon radical with 1–20 carbon atoms (such as alkyl, aryl, aralkyl, etc.). Examples of such hydrocarbon radicals are methyl, ethyl, propyl, butyl, hexyl, decyl, phenyl, benzyl and p-tolyl. R' can also be a substituent which, in addition to or instead of carbon and/or hydrogen, comprises one or more hetero atoms from groups 14–16 of the Periodic Table of the Elements. Thus a substituent can be a group comprising N, O and/or Si.

The R group can be a hydrocarbon group with 1–20 carbon atoms (such as alkylidene, arylidene, arylalkylidene, etc.). Examples of such groups are methylene, ethylene, propylene, butylene, phenylene, with or without a substituted side chain. The R group preferably has the following structure:

$(-ER^2{}_2-)_p$ where p=1–4 and E represents an atom from group 14 of the Periodic Table. The R$^2$ groups can each be H or a group as defined for R'.

Thus the main chain of the R group can also comprise silicon or germanium besides carbon. Examples of such R groups are: dialkyl silylene, dialkyl germylene, tetra-alkyl disilylene or dialkyl silaethylene (—(CH$_2$)(SiR$^2{}_2$)—). The alkyl groups (R$^2$) in such a group preferably have 1 to 4 carbon atoms and more preferably are a methyl or ethyl group.

The DR'$_n$ group comprises a heteroatom D chosen from group 15 or 16 of the Periodic Table of the Elements and one or more substituents R' bound to D. The number of R' groups (n) is coupled to the nature of the hetero atom D, in the sense that n=2 if D originates from group 15 and that n=1 if D originates from group 16. Preferably, the hetero atom D is chosen from the group comprising nitrogen (N), oxygen (O), phosphorus (P) or sulphur (S); more preferably, the hetero atom is nitrogen (N) or phosphorus (P). The R' group is also preferably an alkyl, more preferably an n-alkyl group containing 1–20 C atoms. More preferably, the R' group is an n-alkyl containing 1–10 C atoms. Another possibility is that two R' groups in the DR'$_n$ group are joined to each other to form a ring-type structure (so that the DR'$_n$ group may be a pyrrolidinyl group). The DR'$_n$ group may bond coordinatively to a metal.

In order to prepare such Cp compounds a Cp compound which has been substituted as described in the foregoing can subsequently be substituted with a group of the form —RDR'$_n$, for instance via the following synthesis route.

In a first step of this route a substituted Cp compound is deprotonated by reaction with a base, sodium or potassium.

As base can be applied for instance organolithium compounds (R$^3$Li) or organomagnesium compounds (R$^3$MgX), where R$^3$ is an alkyl, aryl, or aralkyl group and X is a halide, such as for instance n-butyl lithium or i-propylmagnesium chloride. Potassium hydride, sodium hydride, inorganic bases, such as NaOH and KOH, and alcoholates of Li, K and Na can also be used as base. Mixtures of the abovementioned compounds can also be used.

This reaction can be carried out in a polar dispersing agent, such as for instance an ether. Examples of ethers are tetrahydrofuran (THF) and dibutyl ether. Nonpolar solvents, such as for instance toluene, can also be used.

Next, in a second step of the synthesis route the cyclopentadienyl anion obtained reacts with a compound of the formula (R'$_n$D—R—Y) or (X—R—Sul), where D, R, R' and n are as defined in the foregoing. Y is a halogen atom (X) or a sulphonyl group (Sul). The halogen atom X may be for instance chlorine, bromine and iodine. The halogen atom X preferably is a chlorine or bromine atom. The sulphonyl group has the form —OSO$_2$R$^6$, wherein R$^6$ is a hydrocarbon radical containing 1–20 carbon atoms, such as alkyl, aryl, aralkyl. Examples of such hydrocarbon radicals are butane, pentane, hexane, benzene and naphthalene. R$^6$ may also contain one or more hetero atoms from groups 14–17 of the Periodic Table of the Elements, such as N, O, Si or F, in addition to or instead of carbon and/or hydrogen. Examples of sulphonyl groups are: phenylmethanesulphonyl, benzenesulphonyl, 1-butanesulphonyl, 2,5-dichlorobenzenesulphonyl, 5-dimethylamino-1-naphthalenesulphonyl, pentafluorobenzenesulphonyl, p-toluenesulphonyl, trichloromethanesulphonyl, trifluoromethanesulphonyl, 2,4,6-triisopropylbenzenesulphonyl, 2,4,6-trimethylbenzenesulphonyl, 2-mesitylenesulphonyl, methanesulphonyl, 4-methoxybenzenesulphonyl, 1-naphthalenesulphonyl, 2-naphthalenesulphonyl, ethanesulphonyl, 4-fluorobenzenesulphonyl and 1-hexadecanesulphonyl. Preferably, the sulphonyl group is p-toluenesulphonyl or trifluoromethanesulphonyl.

If D is a nitrogen atom and Y is a sulphonyl group, the compound according to the formula (R'$_n$D—R—Y) is formed in situ by reacting an aminoalcohol compound (R'$_2$NR—OH) consecutively with a base (such as described above), potassium or sodium and a sulphonyl halide (Sul-X).

The second reaction step can also be carried out in a polar solvent as described for the first step.

The temperature at which the reaction is carried out is −60 to 80° C. Reactions with X—R—Sul and with R'$_n$D—R—Y in which Y is Br or I are usually carried out at a temperature between −20 and 20° C. Reactions with R'$_n$D—R—Y in which Y is Cl are usually carried out at a higher temperature (10 to 80° C.). The upper limit for the temperature at which the reactions are carried out is determined in part by the boiling point of the compound R'$_n$D—R—Y and that of the solvent used.

After the reaction with a compound of the formula (X—R—Sul) another reaction is carried out with LiDR'$_n$ or HDR'$_n$ in order to replace X by a DR'$_n$ functionality. This reaction is carried out at 20 to 80° C., optionally in the same dispersant as mentioned in the foregoing.

During the synthesis process according to the invention, geminal products may in part be formed. A geminal substitution is a substitution in which the number of substituents increases by 1, but in which the number of substituted carbon atoms does not increase. Geminally substituted Cp compounds are not suitable for use as a ligand and are not considered to be within the scope of the invention. The amount of geminal products formed is low if the synthesis is carried out starting from a substituted Cp compound containing 1 substituent and increases as the substituted Cp compound contains more substituents. If sterically large substituents are present on the substituted Cp compound, geminal products are not, or are scarcely, formed. Examples of sterically large substituents are secondary or tertiary alkyl substituents. The amount of geminal product formed is also low if the second step of the reaction is carried out under the influence of a Lewis base whose conjugated acid has a dissociation constant for which pK$_a$ is less than or equal to −2.5. The pK$_a$ values are based on D. D. Perrin: Dissociation Constants of Organic Bases in Aqueous Solution, International Union of Pure and Applied Chemistry, Butterworths, London 1965. The values have been determined in aqueous H$_2$SO$_4$ solution. Ethers can be mentioned as examples of suitable weak Lewis bases.

If geminal products have formed during the process according to the invention, said products can easily be separated from the nongeminal products by converting the mixture of geminally and nongeminally substituted products into a salt by reaction with potassium, sodium or a base, after which the salt is washed with a dispersant in which the salt of the nongeminal products is insoluble or sparingly soluble. The compounds mentioned above may be used as base.

Suitable dispersants are nonpolar dispersants, such as alkanes. Examples of suitable alkanes are: heptane and hexane.

Metal complexes which are catalytically active if one of their ligands is a compound according to the invention are complexes of metals from groups 4–10 of the Periodic Table of the Elements and rare earths. In this context, complexes of metals from groups 4 and 5 are preferably used as a catalyst component for polymerizing olefins, complexes of metals from groups 6 and 7 in addition also for metathesis and ring-opening metathesis polymerizations, and complexes of metals from groups 8–10 for olefin copolymerizations with polar comonomers, hydrogenations and carbonylations.

Particularly suitable for the polymerization of olefins are such metal complexes in which the metal is chosen from the group consisting of Ti, Zr, Hf, V and Cr. If the metals are not in their highest valency state, it appears that the Cp compounds provide an excellent stability of the complex formed, without blocking the active sites, as a result of which the catalytic activity is higher than when other Cp compounds are used. In the above-mentioned overview article in the J. of Organomet. Chem. from 1994 it is even observed that 'An important feature of these catalyst systems is that tetravalent Ti centres are required for catalytic activity'. In this context it should be kept in mind that Ti is exemplary of the metals that are suitable as metal in the commonly used cyclopentadienyl-substituted metal complexes. The invention therefore also relates to metal complexes in which at least one of the ligands is a substituted Cp compound according to the invention and in which the metal is in a valency state lower than the highest, and to the use of such metal complexes as catalyst for the polymerization of olefins.

The synthesis of metal complexes with the above-described specific Cp compounds as a ligand can take place according to the methods known per se for this purpose. The use of these Cp compounds does not require any adaptations of said known methods.

The polymerization of α-olefins, for example ethene, propene, butene, hexene, octene and mixtures thereof and combinations with dienes, can be carried out in the presence of the metal complexes with the Cp compounds according to the invention as ligand. Suitable in particular for this purpose are complexes of transition metals which are not in their highest valency state, in which just one of the cyclopentadienyl compounds according to the invention is present as ligand and in which the metal is cationic during the polymerization. Said polymerizations can be carried out in the manner known for the purpose and the use of the metal complexes as catalyst component does not make any essential adaptation of these processes necessary. The known polymerizations are carried out in suspension, solution, emulsion, gas phase or as bulk polymerization. The cocatalyst usually applied is an organometal compound, the metal being chosen from Groups 1, 2, 12 or 13 of the Periodic System of the Elements. To be mentioned are for instance alkylaluminooxanes (such as methylaluminoxanes), tris(pentafluorophenyl) borate, dimethylanilinium tetra(pentafluorophenyl) borate or mixtures thereof. The polymerizations are carried out at temperatures between −50° C. and +350° C., more particularly between 25 and 250° C. The pressures used are generally between atmospheric pressure and 250 MPa, for bulk polymerizations more particularly between 50 and 250 MPa, and for the other polymerization processes between 0.5 and 25 MPa. As dispersants and solvents, use may be made of, for example, hydrocarbons, such as pentane, heptane and mixtures thereof. Aromatic, optionally perfluorinated hydrocarbons, are also suitable. The monomer applied in the polymerization can also be used as dispersant or solvent.

The invention will be elucidated by means of the following examples, without being restricted thereto. The synthesis of the catalyst components was performed under dry Ar or $N_2$. For characterization of the products obtained the following analysis methods were used: Gas chromatography was performed on a Hewlett Packard 5890 Series II with an HP Crosslinked Methyl Silicon Gum (25 m×0.32 mm×1.05 μm) column. Gas chromatography combined with mass spectrometry (GC-MS) was performed with a Fisons MD800, equipped with a quadrupole mass detector, autoinjector Fisons AS800 and CPSil8 column (30 m×0.25 mm×1 μm, low bleed). NMR was performed with a Bruker ACP200 ($^1H$=200 MHz; $^{13}C$=50 MHz) or Bruker ARX400 NMR ($^1H$=400 MHz; $^{13}C$=100 MHz). Metal complexes were characterized using a Kratos MS80 mass spectrometer or a Finnigan Mat 4610 mass spectrometer.

EXAMPLE I a. Preparation of tetra(ethyl)cyclopentadiene

A double-walled reactor having a volume of 1 L, provided with baffles, condenser, top stirrer, thermometer and dropping funnel was charged with 1050 g of clear 50% strength NaOH (13.1 mol), followed by cooling to 10° C. Then 32 g of Aliquat 336 (79 mmol) and 51 g (0.77 mol) of freshly cracked cyclopentadiene were added. The reaction mixture was stirred turbulently for a few minutes. Then 344 g of ethyl bromide (3.19 mol) were added gradually in one hour's time, cooling with water taking place at the same time. After 1 hour's stirring at room temperature the reaction mixture was heated to 35° C., followed by a further 6 hours' stirring. Stirring was stopped and phase separation was awaited. The water layer was drawn off and 1050 g (13.1 mol) of fresh 50% strength NaOH were added, followed by a further 5 hours' stirring at room temperature. GC was used to show that at that instant 15% tri-, 78% tetra- and 7% of penta (ethyl)cyclopentadiene were present in the mixture. The product was distilled at 11 mbar and 91° C. After distillation, 74.8 g of tetra(ethyl)cyclopentadiene were obtained. Characterization took place with the aid of GC, GC-MS, $^{13}C$- and $^1H$-NMR.

b. Preparation of (dimethylaminoethyl)tetraethylcyclopentadiene

A solution of n-butyllithium in hexane (6.00 ml; 1.65 mol/l; 9.90 mmol) was added dropwise to a solution of tetraethylcyclopentadiene (2.066 g; 11.6 mmol) in dry THF (20 ml) in a Schlenk vessel at room temperature.

Then a solution of n-butyllithium in hexane (5.90 ml; 1.65 mol/l; 9.74 mmol) was added dropwise to a cold solution (−78° C.) of 2-dimethylaminoethanol (0.867 g; 9.74 mmol) in THF (35 ml) in a second Schlenk vessel. After stirring for two hours at room temperature, the mixture was again cooled to −78° C. and the solid p-toluenesulphonyl chloride (1.855 g; 9.74 mmol) was added slowly. The mixture was brought to 0° C. and stirred at that temperature for 5 minutes, after which the mixture from the first Schlenk vessel was added all at once. After 16 hours, the conversion was 100%. After column chromatography, 2.6 g of (dimethylaminoethyl)tetraethylcyclopentadiene was obtained. The geminal isomers were isolated from the nongeminal isomers by converting the nongeminal isomers into their sparingly soluble potassium salt and then washing this salt with a solvent in which it does not or only sparingly dissolve.

c. Synthesis of 1-(dimethylaminoethyl)-2,3,4,5-tetraethylcyclopentadienyltitanium (III) dichloride and [1-(dimethylaminoethyl)-2,3,4,5-tetraethylcyclopentadienyl]dimethyltitanium(III) [$C_5(Et)_4(CH_2)_2NMe_2Ti(III)Cl_2$] and [$C_5(Et)_4(CH_2)_2NMe_2Ti(III)Me_2$]

In a Schlenk vessel 0.38 g (1.523 mmol) of dimethylaminoethyltetraethylcyclopentadiene were dissolved in 20 mL of diethyl ether, after which the solution was cooled to −60° C. Then 0.95 mL of n-butyllithium (1.6M in hexane; 1.52 mmol) were added dropwise. After 30 minutes, cooling was stopped, while stirring was continued for one more hour at room temperature. In a second Schlenk vessel 30 mL of tetrahydrofuran were added to 0.57 g of Ti(III)Cl$_3$.3THF (1.538 mmol). Both Schlenk vessels were cooled to −60° C., after which the organolithium compound was added to the Ti(III)Cl$_3$ suspension. The reaction mixture was then stirred for 18 hours at room temperature, after which the solvent was evaporated. 50 mL of petroleum ether were added to the residue, which was then boiled down again. The residue was a solid substance containing 1-(dimethylaminoethyl)-2,3,4,5-tetraethylcyclopentadienyltitanium(III)dichloride. To 0.25 g (0.68 mmol) of the product, 20 mL of diethyl ether was added. After cooling to −60° C., 0.85 mL of methyllithium (1.6 M in diethyl ether; 1.36 mmol) was added. After 3 hours' stirring at room temperature the solvent was removed at reduced pressure. After addition of petroleum ether, filtration and boiling down, 0.17 g of a dark oil was obtained, containing 1-[(dimethylaminoethyl)-2,3,4,5-tetraethylcyclopentadienyl]dimethyltitanium(III).

EXAMPLE II a. Preparation of tetra(octyl)cyclopentadiene

A double-walled reactor having a volume of 1.5 L, provided with baffles, condenser, top stirrer, thermometer and dropping funnel was charged with 900 g of clear 50% strength NaOH (11.3 mol), followed by cooling to 10° C. Then 30 g of Aliquat 336 (74 mmol) and 48 g (0.72 mol) of freshly cracked cyclopentadiene were added. The reaction mixture was stirred turbulently for a few minutes. Then 577 g of octyl bromide (2.99 mol) were added in one hour's time, cooling with water taking place at the same time. After 1 hour's stirring at room temperature the reaction mixture was heated to 35° C., followed by a further 6 hours' stirring. Stirring was stopped and phase separation was awaited. The water layer was drawn off and 920 g (11.5 mol) of fresh 50% strength NaOH were added, followed by a further 5 hours' stirring at room temperature. GC was used to show that at that instant 10% of tri-, 83% of tetra- and 7% of penta(octyl) cyclopentadiene were present in the mixture. The product was distilled at reduced pressure. After vacuum distillation, 226.6 g of tetra(octyl)cyclopentadiene were obtained. Characterization of the product took place with the aid of GC, GC-MS, $^{13}$C- and $^{1}$H-NMR.

b: Preparation of (dimethylaminoethyl)tetra(n-octyl) cyclopentadiene

A solution of n-butyllithium in hexane (24.8 ml; 1.6 mol/l; 39.6 mmol) was added dropwise at room temperature to a solution of tetra(n-octyl)cyclopentadiene (20.4 g; 39.6 mmol) in dry THF (100 ml) in a Schlenk vessel.

Then a solution of n-butyllithium in hexane (24.6 ml; 1.6 mol/l; 39.6 mmol) was added dropwise to a cold solution (−78° C.) of 2-dimethylaminoethanol (3.53 g; 39.6 mmol) in THF (30 ml) in a second Schlenk vessel. After stirring for two hours at room temperature, the mixture was again cooled to −78° C. and the solid tosyl chloride (7.54 g; 39.6 mmol) was added slowly. The mixture was brought to 0° C. and stirred at that temperature for 5 minutes, after which the mixture from the first Schlenk vessel was added at once. After 16 hours, the conversion was 87%. After column chromatography, 19.2 g of (dimethylaminoethyl)tetra(n-octyl)cyclopentadiene were obtained. The geminal isomers were isolated from the nongeminal isomers by converting the nongeminal isomers into their sparingly soluble potassium salt and then washing this salt with a solvent in which it does not or only sparingly dissolve.

EXAMPLE III a. Preparation of tetra(n-propyl)cyclopentadiene

A double-walled reactor having a capacity of 1 l and provided with a baffle, condenser, top stirrer, thermometer and dropping funnel was filled with 1000 g (12.5 mol) of clear 50% NaOH, after which the mixture was cooled to 10° C. Then 30 g (74 mmol) of Aliquat 336 and 50 g (0.75 mol) of freshly cracked cyclopentadiene were added. The reaction mixture was vigorously stirred for several minutes. Then 373 g (3.03 mol) of propyl bromide were added in one hour. During this process, the mixture was cooled with water. After stirring for 1 hour at room temperature, the reaction mixture was heated to 35° C., after which stirring was carried out again for 6 hours. Stirring was stopped and phase separation was awaited. The water layer was drained off and 990 g (12.4 mol) of fresh 50% NaOH were added. Then stirring was carried out for a further 5 hours at room temperature. It was demonstrated with GC that 14% tri-, 80% tetra- and 6% pentapropylcyclopentadiene were present in the mixture at that instant. The product was distilled under reduced pressure. After vacuum distillation, 103.1 g of tetrapropylcyclopentadiene were obtained.

The product was characterized with the aid of GC, GC-MS, $^{13}$C- and $^{1}$H-NMR.

b: Preparation of (dimethylaminoethyl)tetra(n-propyl)cyclopentadiene

A solution of n-butyllithium in hexane (93.8 ml; 1.6 mol/l; 150 mmol) was added dropwise to a solution of tetra(n-propyl)cyclopentadiene (35.0 g; 150 mmol) in dry THF (200 ml) at room temperature in a 500 ml three-neck flask.

Then a solution of n-butyllithium in hexane (93.8 ml; 1.6 mol/l; 150 mmol) was added dropwise to a cold solution (−78° C.) of 2-dimethylaminoethanol (13.35 g; 150 mmol) in THF (100 ml) in a second Schlenk vessel. After stirring for 2 hours at room temperature, the mixture was again cooled to −78° C. and the solid tosyl chloride (28.5 g; 150 mmol) was added slowly. The mixture was brought to −20° C. and stirred at that temperature for 5 minutes, after which the mixture from the three-neck flask was added. After 16 hours, the conversion was 97%. After column chromatography, 39.6 g of (dimethylaminoethyl)tetra(n-propyl)cyclopentadiene was obtained.

The geminal isomers were isolated from the nongeminal isomers by converting the nongeminal isomers into their sparingly soluble potassium salt and then washing this salt with a solvent in which it does not or only sparingly dissolve.

c. Synthesis of 1-(dimethylaminoethyl)-2,3,4,5-tetra-n-propylcyclopentadienyltitanium(III) dichloride and [1-(dimethylaminoethyl)-2,3,4,5-tetra-n-propylcyclopentadienyl]dimethyltitanium(III) [C$_5$(n-Pr)$_4$(CH$_2$)$_2$NMe$_2$Ti(III)Cl$_2$] and [C$_5$(n-Pr)$_4$(CH$_2$)$_2$NMe$_2$Ti(III)Me$_2$]

In a Schlenk vessel 0.62 g (2.03 mmol) of dimethylaminoethyltetraethylcyclopentadiene was dissolved in 20 mL of diethyl ether, after which the solution was cooled to −60° C. Then 1.27 mL of n-butyllithium (1.6M in hexane; 2.03 mmol) were added dropwise. After 30 minutes, cooling was stopped, while stirring was continued for one more hour at room temperature. In a second Schlenk vessel 30 mL of tetrahydrofuran were added to 0.75 g of Ti(III)Cl$_3$.3THF (2.03 mmol). Both Schlenk vessels were cooled to −60° C., after which the organolithium compound was added to the Ti(III)Cl$_3$ suspension. The reaction mixture was then stirred for 18 hours at room temperature, after which the solvent was evaporated. 50 mL of petroleum ether were added to the residue, which was then boiled down again. The residue was a oil containing 1-(dimethylaminoethyl)-2,3,4,5-tetra-n-propylcyclopentadienyltitanium(III)dichloride. To 0.51 g (1.01 mmol) of the product, 20 mL of diethyl ether was added. After cooling to −60° C., 1.26 mL of methyllithium (1.6 M in diethyl ether; 2.02 mmol) was added. After 3 hours' stirring at room temperature the solvent was removed at reduced pressure. After addition of petroleum ether, filtration and boiling down, 0.31 g of a dark oil was obtained, containing 1-[(dimethylaminoethyl)-2,3,4,5-tetra-n-propylcyclopentadienyl]dimethyltitanium(III).

COMPARATIVE EXPERIMENT A

Preparation of ((dimethylaminoethyl) cyclopentadienyl)titaniumdichloride

The synthesis was carried out as in Example I, but now starting from: 1.37 g of (dimethylaminoethyl) cyclopentadiene (10 mmol), 6,2 mL of a 1.6M butyllithium solution in hexane, 3.7 g of $TiCl_3.3THF$ (10 mmol). 2.03 g og (dimethylaminoethyl)cyclopentadienyl) titaniumdichloride was obtained.

POLYMERIZATION EXAMPLES IV–X AND COMPARATIVE EXPERIMENTS B AND C

A. The copolymerization of ethene with propene was carried out as follows:

Under dry nitrogen a 1-liter stainless steel reactor was filled with 400 ml of pentamethyl heptane (PMH) and 30 μmol of triethyl aluminium (TEA) or trioctyl aluminium (TOA) as scavenger. The reactor was pressurized to 0.9 MPa with purified monomers and so conditioned that the propene:ethene ratio in the gas above the PMH was 1:1. The reactor contents were brought to the required temperature with stirring.

After conditioning of the reactor the metal complex (5 μmol) to be used as catalyst component and the cocatalyst (30 μmol $BF_{20}$) were pre-mixed for 1 minute and supplied to the reactor with the aid of a pump. The mixture was pre-mixed in about 25 ml of PMH in a catalyst dispensing vessel and purged with about 75 ml of PMH, all under a dry nitrogen flow.

During the polymerization the monomer concentrations were kept constant as much as possible by supplying propene (125 N-liters/h) and ethene (125 N-liters/h) to the reactor. The reaction was followed by monitoring the course of the temperature and the monomer supply.

After 10 minutes' polymerization the monomer supply was stopped and the solution was drained off under pressure and collected. The polymer was dried under vacuum for 16 hours at about 120° C.

B. The homopolymerization of ethene and the copolymerization of ethene with octene were carried out as follows:

600 ml of an alkane mixture (pentamethyl heptane or special boiling range solvent were supplied to a 1.5-liter stainless steel reactor under dry nitrogen as reaction medium. Then the envisaged amount of dry octene (which may also be nil) was introduced into the reactor. Next the reactor was heated to the required temperature with stirring under the required ethene pressure.

25 ml of the alkane mixture as solvent were supplied to a 100-ml catalyst dispensing vessel. In this vessel the required amount of an Al-containing cocatalyst was pre-mixed for 1 minute with the required amount of metal complex such that the Al/(metal in the complex) was equal to 2000.

This mixture was then supplied to the reactor and the polymerization started. The polymerization reaction was carried out isothermally. The ethylene pressure was kept constant at the set pressure. Upon completion of the required reaction time the ethene supply was stopped and the reaction mixture was drained off and quenched with methanol.

The reaction mixture with methanol was washed with water and HCl in order to remove the catalyst residues. Then the mixture was neutralized with $NaHCO_3$. Next, an antioxidant (Irganox 1076, TM) was added to the organic fraction for the purpose of stabilization of the polymer. The polymer was dried under vacuum at 70° C. for 24 hours.

In both cases the following conditions were varied:
metal complex
type and amount of scavenger
type and amount of cocatalyst
temperature The actual conditions of each case are stated in Table I.

TABLE I

| Example | cat. complex obtained in ex.: | amount of complex (μmol/0.51) | temp. (° C.) and press. (bar) | scavenger | amount of scavenger (mmol/0.51) | co-cat.* | ratio Al/M or B/M | sec. monomer | yield (kg/gM* 5 min.) | incorp. co-monomer (m %) |
|---|---|---|---|---|---|---|---|---|---|---|
| IV | I | 10 | 80 / 8 | — | — | MAO | 2000 | 18 g. oc-tene | 91 | 19 |
| V | I | 10 | 120 / 8 | — | 0.4 | MAO | 2000 | 18 g. oc-tene | 16 | 33.5 |
| VI | I | 10 | 150 / 20 | TOA | — | BF2O | 2 | 18 g. oc-tene | 16.6 | N.D.[1] |
| VII | III | 10 | 80 / 8 | — | — | MAO | 2000 | 18 g. oc-tene | 113 | N.D. |
| VIII | III | 10 | 120 / 8 | — | — | MAO | 2000 | 18 g. oc-tene | 20 | N.D. |
| IX | II | 10 | 80 / 8 | — | — | MAO | 2000 | 18 g. oc-tene | 105 | N.D. |
| X | II | 10 | 120 / 8 | — | — | MAO | 2000 | 18 g. oc-tene | 24 | N.D. |
| B | A | 10 | 120 / 8 | — | — | MAO | 2000 | 18 g. oc-tene | 8 | N.D. |
| C | A | 10 | 135 / 8 | — | — | MAO | 2000 | 18 g. oc-tene | 0 | N.D. |

*BF2O: tetrakis(pentaphenylborate)
MAO: methylaluminoxane from Witco
[1] N.D. = not determined

What is claimed is:

1. A metal complex comprising as a ligand at least one cyclopentadienyl group derived from a polysubstituted cyclopentadiene ring compound wherein at least one substituent on the cyclopentadiene ring is represented by the formula $-RDR'_n$, wherein R is a bonding group between the cyclopentadiene ring and the $DR'_n$ group, D is a hetero atom chosen from group 15 or 16 of the Periodic Table of the Elements, R' is a substituent on the hetero atom, and n is the number of R' groups bonded to D wherein if D originates from group 15 then n=2, and if D originates from group 16 then n=1, and wherein each R' comprises at least one member independently selected from the group consisting of hydrocarbon radicals of 1 to 20 carbon atoms which may comprise one or more hetero atoms selected from groups 14, 15, or 16 of the Periodic Table, wherein at least one further substituent on the cyclopentadiene ring is a linear alkyl group comprising at least two carbon atoms, and wherein the metal is titanium (III).

2. A metal complex according to claim 1, wherein at least two linear alkyl groups each comprising at least two carbon atoms are present as substituents on the cyclopentadienyl ring.

3. A metal complex according to claim 1, wherein two or three linear alkyl groups each comprising at least two carbon atoms are present as substitents on the cyclopentadienyl ring.

4. A metal complex according to claim 1, wherein said linear alkyl groups are each independently selected from the group consisting of ethyl groups and propyl groups.

5. A process for the polymerization of α-olefins comprising at least one catalyst component a metal complex according to claim 1.

6. A process for the polymerization of ethylene comprising at least one catalyst component a metal complex according to claim 1.

* * * * *